United States Patent
Ning et al.

[19]

[11] Patent Number: 5,999,587
[45] Date of Patent: Dec. 7, 1999

[54] METHOD OF AND SYSTEM FOR CONE-BEAM TOMOGRAPHY RECONSTRUCTION

[75] Inventors: Ruola Ning, Penfield; Xiaohui Wang, Rochester, both of N.Y.

[73] Assignee: University of Rochester, Rochester, N.Y.

[21] Appl. No.: 08/888,331

[22] Filed: Jul. 3, 1997

[51] Int. Cl.[6] .................................................. A61B 6/03
[52] U.S. Cl. ............................................. 378/4; 378/901
[58] Field of Search ........................................ 378/4, 901

[56] References Cited

U.S. PATENT DOCUMENTS

| | | | |
|---|---|---|---|
| 5,170,439 | 12/1992 | Zeng et al. | 382/131 |
| 5,257,183 | 10/1993 | Tam | 378/4 |
| 5,278,884 | 1/1994 | Eberhard et al. | 378/4 |
| 5,365,560 | 11/1994 | Tam | 378/8 |
| 5,390,226 | 2/1995 | Tam | 378/19 |
| 5,400,255 | 3/1995 | Hu | 378/4 |
| 5,461,650 | 10/1995 | Tam | 378/4 |
| 5,517,602 | 5/1996 | Natarajan | 345/419 |

OTHER PUBLICATIONS

Smith, Bruce D., "Image Reconstruction from Cone–Beam Projections: Necessary and Sufficient Conditions and Reconstruction Methods", IEEE Transactions on Medical Imaging, vol. MI–4, No. 1, pp. 14–25, Mar. 1985.

P. Grangeat, "Mathematical Framework of Cone Beam 3D Reconstruction via the First Derivative of the radon Transform", *Mathematical Methods in Tomography*, Herman, Lewis, Natterer (eds.) Lecture Notes in Mathematics, No. 1497, pp. 66–97, Spring Verlag (1990).

L. A. Feldkamp et al., "Practical cone–beam algorithm", J. Opt. Soc. Am. A/vol. 1, No. 6, Jun. 1984 pp. 612–619.

Y. Weng et al., "A Reconstruction Algorithm for Helical Cone–Beam SPECT", IEEE Transactions on Nuclear Science, vol. 40, No. 4, Aug. 1993, pp. 1092–1101.

B. Smith, "Cone–beam tomography: recent advances and a tutorial review", Optical Engineering, vol. 29, No. 5, May 1990, pp. 524–534.

H. Tuy, "An inversion formula for cone–beam reconstruction", SIAM J. Appl. Math, vol. 43, No. 3, Jun. 1983, pp. 546–552.

*Primary Examiner*—David Vernon Bruce
*Attorney, Agent, or Firm*—Blank Rome Comisky & McCauley LLP

[57] ABSTRACT

A method of and system for the 3-D reconstruction of an image from 2-D cone-beam tomography projections is disclosed in which a circle-plus-arc data acquisition geometry is utilized to provide a complete set of data so that an exact 3-D reconstruction is obtained. A volume CT scanner which uses a cone-beam x-ray source and a 2-D detector is utilized in which one set of cone-beam projections is acquired while rotating the x-ray tube and detector on the CT gantry and then another set of projections is acquired while tilting the gantry by a small angle. The projection data is preweighted and the partial derivatives of the preweighted projection data are calculated. Those calculated partial derivatives are rebinned to the first derivative of the Radon transform, for both the circular orbit data and the arc orbit data. The second partial derivative of the Radon transform is then calculated and then the reconstructed 3-D images are obtained by backprojecting using the inverse Radon transform.

27 Claims, 4 Drawing Sheets

METHOD OF AND SYSTEM FOR CONE-BEAM TOMOGRAPHY RECONSTRUCTION

BACKGROUND OF THE INVENTION

The present invention is directed to a method of and system for computed tomography (CT) density image reconstruction. More particularly, the present invention is directed to the three-dimensional reconstruction from two-dimensional projections acquired with x-ray cone-beam CT and single photon emission computed tomography (SPECT) scanners.

For about the past twenty years, computerized tomography has revolutionized diagnostic imaging systems as well as non-destructive test imaging techniques. Conventional CT scanners use a fan-shaped x-ray beam and one-dimensional detector in order to reconstruct a single slice with a single scan of an object. However, current CT technology is limited by a trade-off between high longitudinal resolution and fast volume scanning. One method which has been utilized to address the shortcomings of CT scanner technology is the use of cone-beam tomography. A cone-beam volume CT scanner uses a cone-beam x-ray source and a two-dimensional detector to reconstruct the whole volume of an object with a single scan of that object. The data obtained from the scan of the object is processed in order to construct an image that presents a two-dimensional slice taken through the object. The current technique for reconstructing an image from 2-D is referred to in the art as the filtered back projection technique. That process converts the attenuation measurements from a scan into integers called "CT numbers" or "Hounsfield H units" which are then used to control the brightness of a corresponding pixel on a cathode ray display.

In a 3-D scan technique, a cone-shaped x-ray beam is used which diverges to form a cone-beam that passes through the object and impinges on a two-dimensional array of detector elements. In that manner, the volume scanning time of a 3-D object can be at least 10 times shorter than a standard CT on a spiral CT. In contrast to existing CT with a through plane resolution of 1.0 lp.mm, the reconstructions of cone beam CT will have isotropic spatial resolution along all three axes (0.5–2.0 lp.mm). Each view is thus a 2-D array of x-ray attenuation measurements and the complete scan produces a 3-D array of attenuation measurements.

At present, either of two methods are commonly used to reconstruct a set of images from the acquired 2-D attenuation measurements. The first technique is that developed by Feldkamp, Davis & Kress, which is described in "Practical Cone-Beam Algorithm", *J. Opt. Soc. Am.*, Vol. I, pp. 612–619 (1984). The Feldkamp, et al. technique, which uses an algorithm which was derived using approximations of a tiered fan beam formula, is a convolution-back projection method which operates directly on the line integrals of the actual attenuation measurements. That method can be easily implemented with currently available hardware and is a good reconstruction for images at the center or "mid-plane" of the cone-beam. While the algorithm of Feldkamp, et al. provides excellent computational efficiency and minimal mechanical complexity in data acquisition, its major shortcoming is that it is based on single circle cone-beam geometry. Single circle cone-beam geometry, in which the source always lies on a circle, cannot provide a complete set of data to exactly reconstruct the object. For that reason, Feldkamp, et al.'s algorithm causes some unavoidable distortion in the non-central transverse planes, as well as resolution degradation in the longitudinal direction.

In order to address the problems of Feldkamp's algorithm, several other approaches have been proposed using different cone-beam geometries including dual orthogonal circles, helical orbit, orthogonal circle-and-line, and Smith's curve. Such geometries can achieve exact reconstructions when using the approach of Tuy, Smith, or Gangreat.

In addition to the Feldkamp, et al. approach for analytic cone-beam reconstruction, a second commonly used method is that disclosed by Pierre Grangeat in, "Mathematical Framework of Cone-Beam 3-D Reconstruction Via the First Derivative of the Radon Transform", *Mathematical Methods in Tomography*, Herman, Lewis, Natterer (eds.) Lecture Notes in Mathematics, No. 1497, pp. 66–97, Spring Verlag (1991). That algorithm provides an accurate solution to the image reconstruction task based on a fundamental relationship between the derivative of the cone-beam plane integral through the derivative of the parallel beam plane integral. While the Grangeat method is theoretically accurate, it requires mathematical operations that can be solved only using finite numerical calculations that are approximations. Thus, errors can be introduced by the implementation of the Gangreat method that can be greater than those produced using the Feldkamp, et al. method and such errors are not correlated with the cone-beam angle.

A third method has been disclosed by H. K. Tuy in "An Inversion Formula for a Cone-Beam Reconstruction", *SAIM J. Appl. Math.* 43, pp. 546–552 (1983). Using Tuy's approach, in order to generate a complete or sufficient set of data, every plane which passes through the imaging field of view must also cut through the orbit of the focal point at least once. The single plane or orbit of Feldkamp, et al. does not satisfy this condition.

Still yet another approach that has been proposed is the inversion of the cone-beam data sets if the assumption is made that for any line that contains a vertex point and a reconstruction point, there is an integer M which remains constant for the line such that almost every plane that contains this line intersects the geometry exactly M times. Mathematical improvement to the reconstruction algorithms was described in an article by B. D. Smith entitled "Cone-Beam Tomography: Recent Advances and a Tutorial Review," *Opt. Eng.*, Vol. 29 (5) pp. 524–534 (1990). However, such an integer requirement condition is too restrictive for practical application since the only known source point geometry which meets that condition is a straight line.

Two somewhat recent patents were issued in the United States directed to the cone-beam reconstruction problem. The first, U.S. Pat. No. 5,170,439 to Zeng, et al., was issued on Dec. 8, 1992 and utilizes the above-described cone-beam reconstruction method using combined circle and line orbits. However, that technique requires the removal of redundant and unnecessary data, which necessarily requires more computing time and complexity than the method and system of the present invention.

Another approach to the reconstruction of images from cone-beam data is disclosed in U.S. Pat. No. 5,400,255, which issued to Hu on Mar. 21, 1995. The methodology disclosed in the Hu patent represents a minimal improvement from Feldkamp's algorithm and it is still an approximate method based on a single circle cone beam geometry. It cannot result in exact reconstruction and it is not acceptable in many clinical applications when the cone angle is large.

In contrast to the prior art approaches, the present invention discloses an exact cone-beam reconstruction system and method using a circle-plus-arc data acquisition geometry in which the locus of a source and a detector is a circle plus an orthogonal arc. In that manner, the best image quality of a cone-beam volume CT is achieved without introducing any additional mechanical complexity compared to a regular CT gantry. If the locus of an x-ray source and a detector is a single circle during cone-beam scanning (single circle cone-beam geometry), an incomplete set of projection data will be acquired. The incompleteness of the projection data results in some unavoidable blurring in the planes away from the central z plane and a resolution loss in the z direction (i.e., Feldkamp, et al.'s algorithm). The reconstruction error due to the incompleteness of the projection data could be up to 40 Hounsfield units (HU) when using Feldkamp, et al.'s algorithm with an 11° cone angle. However, using the data acquisition geometry of the present invention, the locus of an x-ray source and a detector is a circle plus an arc perpendicular to the circle. That corresponds to rotating the x-ray tube and detector on the gantry, and then acquiring the arc projections on a perpendicular arc while tilting the gantry at a relatively small angle (±15° to ±30°). Such geometry results in a complete set of data for an object with a 25–40 cm diameter, which corresponds to a 37–60 cm field size at the detector with a magnification of 1.5. Using the system and method of the present invention, the 3-D reconstruction is exact and no image blurring or resolution loss occurs.

The method and system of the present invention is based upon the three-dimensional Radon transform. The algorithm used with the present invention first transforms the cone-beam projections acquired from a circle-arc orbit into the first derivative of the 3-D Radon transform of an object using Grangeat's formula. Then, the object function is reconstructed using the inverse Radon transform. In order to reduce the interpolation errors in the re-binning process required by Grangeat's formula, new re-binning equations have been derived exactly, therefore transforming 3-D interpolations into one-dimensional interpolations. The inventive cone-beam acquisition method and system disclosed herein provides a complete set of projection data such that the cone-beam image reconstruction algorithm achieves exact reconstructions. The result is a 3-D cone-beam reconstruction which introduces no obvious artifacts and only a practical acceptable reduction of reconstruction accuracy.

SUMMARY AND OBJECTS OF THE INVENTION

Figure 1:
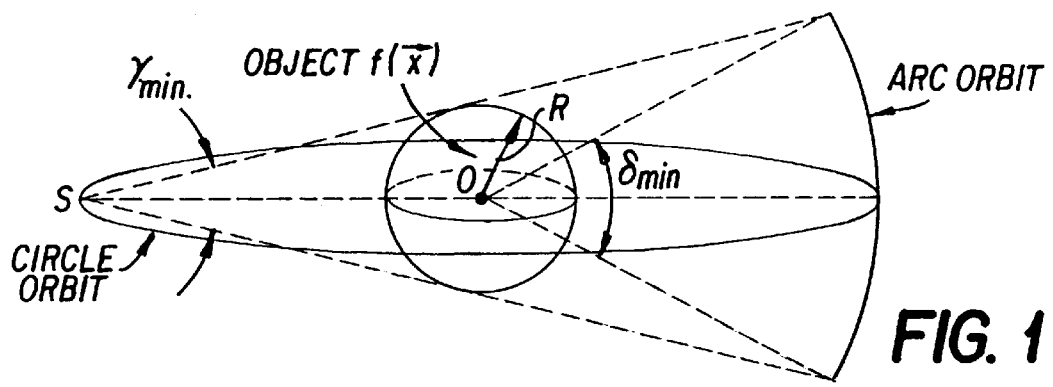
FIG. 1 is a drawing showing the geometry of the circle-plus-arc orbit utilized by the present invention.

In view of the foregoing, it should be apparent that there still exists a need in the art for a method of and apparatus for producing a 3-D image from two dimensional projections acquired with x-ray cone-beam volume CT and SPECT scanners such that exact reconstructions with no image blurring or distortion are produced. It is, therefore, a primary object of this invention to provide a method of and apparatus for obtaining an exact 3-D reconstruction from 2-D projections acquired with cone-beam volume CT and SPECT scanners which is characterized by lack of image blurring and distortion.

More particularly, it is an object of this invention to provide a new method for cone-beam reconstruction using a circle-plus-arc data acquisition geometry to provide a complete set of data such that an exact 3-D reconstruction can be obtained using a cone-beam x-ray source and a 2-D detector with a conventional CT scanner gantry.

Still more particularly, it is an object of this invention to provide for a circle-plus-arc data acquisition geometry for use with volume CT scanner using a cone-beam x-ray source and a 2-D detector in which a standard CT gantry is utilized without introducing mechanical complexity to achieve exact 3-D reconstructions of an object.

Briefly described, these and other objects of the invention are accomplished by the use of a new analytic cone-beam reconstruction algorithm which uses a circle-plus-arc data acquisition geometry to provide a complete set of data so that an exact 3-D reconstruction is obtained even in cases where Feldkamp's algorithm fails severely. The novel data acquisition scheme disclosed herein is applied to a volume CT scanner which uses a cone-beam x-ray source and a 2-D detector, such as a selenium or silicon thin-film flat-panel x-ray imager. The circle-plus-arc data acquisition scheme is implemented by acquiring one set of cone-beam projections while rotating an x-ray tube and a detector on a standard CT gantry and, then, acquiring another set of projections while tilting the gantry by a small angle of approximately ±15° to approximately ±30° with the x-ray tube and the detector fixed on the gantry. That scanning method is accomplished on a standard CT gantry without introducing mechanical complexity and achieves exact 3-D reconstructions of an object with a 25–40 cm diameter.

In practice, the arc length and arc sampling rate can be reduced (for example, by 50%) without the introduction of any obvious artifacts and with only a practically acceptable reduction of reconstruction accuracy. Thus, data acquisition time on the arc is significantly reduced by decreasing the arc length or arc sampling rate with the result that the desired 3-D image reconstruction may be computed in less time.

In its method aspects, the present invention is carried out by first obtaining the cone-beam projection data from a volume CT or SPECT scanner. Then, that projection data is preweighted and the partial derivatives of the preweighted projection data are calculated. Next, the calculated partial derivatives are rebinned to the first derivative of the Radon transform, for both the circular orbit data and the arc orbit data. The second partial derivative of the Radon transform is then calculated. Finally, the reconstructed 3-D images are obtained by backprojecting using the inverse Radon transform.

With these and other objects, advantages and features of the invention that may become hereinafter apparent, the nature of the invention may be more clearly understood by reference to the following detailed description of the invention, the appended claims and to the several drawings attached herein.

DETAILED DESCRIPTION OF THE PREFERRED EMBODIMENT

The following description of the theoretical underpinnings of the present invention is provided for background purposes.

As described above, this invention is directed to a method of and an apparatus for cone-beam tomography, which allows the processing of projection data which will be described herein to provide an artifacts-free reconstruction of a 3-D image.

In cone-beam tomography, the data sufficient condition must be fulfilled in order to obtain exact 3-D reconstructions. Tuy showed that the sufficient data condition requires that each plane passing through an object intersect the orbit of the focal point. In fact, dual orthogonal circles, orthogonal circle-and-line, and a helical orbit all satisfy Tuy's data sufficient condition for exact 3-D reconstructions. However, a single circular orbit does not, because planes parallel to the circular orbit do not contain any focal points on the orbit. In the present invention, a combination of a circular orbit and a small arc orbit is used. As shown in FIG. 1, the plane of the arc orbit is perpendicular to the circular orbit, and the two orbits intersect at the center of the arc. It is assumed that the two orbits are concentric at point O, and therefore have the same radius D (being concentric is assumed for the simplicity of mathematical derivation). The introduction of the arc orbit provides focal points for the planes which will not intersect the circular orbit. It is also assumed that the object function $f(\vec{x})$ has a finite boundary.

One extreme situation to the circle-plus-arc orbit is that the arc extends to a whole circle, therefore constructing two orthogonal circles. In that case, the radius R of the sphere that constrains the object function $f(\vec{x})$ has to satisfy the inequality:

$$D >= \sqrt{2} R. \tag{1}$$

As shown in FIG. 1, the cone-beam originating from point S should fully cover the object, i.e., $$\gamma_{min} \geq 2\sin^{-1}\left(\frac{R}{D}\right), \tag{2}$$

where D is the radius of the circular orbit and $\gamma_{min}$ is the minimum required cone-angle.

In order to satisfy Tuy's data sufficient condition theorem, the arc orbit should supply focal points to planes which will not intersect the circular orbit. The outer-most one of those planes is tangential to both the circular orbit and the sphere of radius R which constrains the object and is perpendicular to the arc orbit plane. If the minimum arc spanning angle is represented as $\delta_{min}$, then from the geometry shown in FIG. 1, it follows that the inequality below should be satisfied:

$$\delta_{min} \geq 2\gamma_{min} \geq 4\sin^{-1}\left(\frac{R}{D}\right). \tag{3}$$

The inequalities 2 and 3 guarantee that any plane that intersects the object will also intersect either the circular orbit or the arc orbit, therefore providing the data sufficient condition. Thus, the minimum spanning angle of the arc orbit should be no less than two times the minimum cone-angle.

The cone-beam projections and the 3-D Radon transform of an object will now be expressed in terms of the coordinate systems defined in this application. The cone-beam geometry is shown and defined in FIG. 2.

Figure 2:
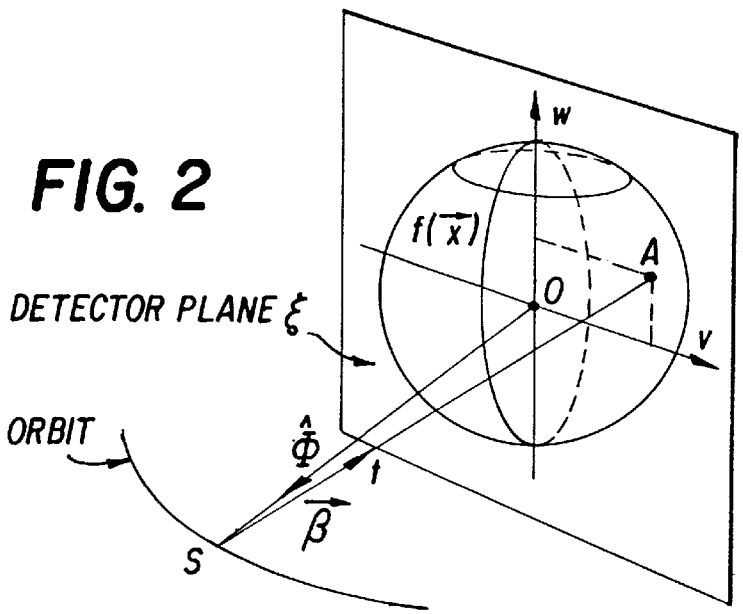
FIG. 2 is a drawing of the cone-beam geometry as used in connection with the present invention.

In the 3-D spatial space shown in FIG. 2, the point O is the origin of the coordinate system and $\vec{OS}=\vec{\Phi}$ is the position vector of the cone-beam focal point S. For purposes of the discussion herein, it will simplify mathematical derivation if the detector plane $\xi$ is defined in such a way that $\xi$ is perpendicular to the vector $\vec{OS}$ and always contains the point O. That convention will be used throughout this specification. Also, point A is any point in the detector plane and $\hat{\beta}$ is the unit directional vector of $\vec{SA}$.

In FIG. 2, a local detector Cartesian coordinate system uvw-O is also defined. The u-axis is coincident with the vector $\vec{OS}$ and the v-axis and w-axis are in the detector plane $\xi$ ($\vec{\Phi}$). Those local coordinates are discussed later herein in connection with the formula developed by Grangeat.

Cone-beam projections are generally defined as line integrals. If the object is characterized by some function $f(\vec{x})$, $\vec{x} \in R^3$, the cone-beam projection g of that object can be expressed as:

$$g(\vec{\Phi}, \hat{\beta}) = \int_{-\infty}^{+\infty} f(\vec{\Phi} + t\hat{\beta}) dt, \tag{4}$$

where $\hat{\beta}$ is also called the directional vector along the ray of the line integral.

Figure 3:
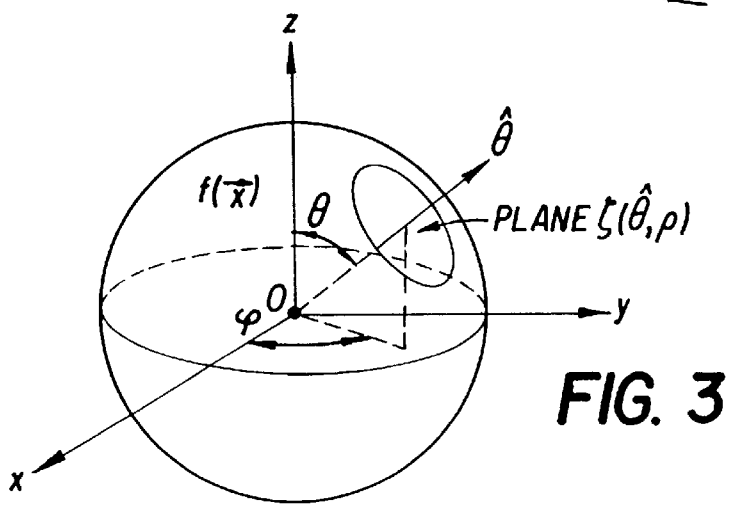
FIG. 3 is a drawing of the Radon transform geometry as used in connection with the present invention.

The Radon transform of a 3-D object is defined as plane integrals. Thus, the radon transform are integrals of the object function $f(\vec{x})$ in the planes $\zeta(\hat{\theta},\rho)$, where $\hat{\theta}$ is the normal vector of the plane $\zeta$ and $\rho$ is the distance from the plane $\zeta$ to the origin of the coordinates, point O. In the 3-D Cartesian space as shown in FIG. 3, any plane $\zeta$ can be uniquely defined by a unit vector $\hat{\theta}$ and a scalar $\rho$. Thus, $$\hat{\theta} = (\sin \theta \cos \phi, \sin \theta \sin \phi, \cos \theta), \tag{5}$$

is the normal vector to the plane $\zeta(\hat{\theta},\rho)$ and $\rho$ is the distance from that plane to the origin O of the coordinate system, $\theta \in [0, \pi)$, $\phi \in [0, \pi)$ and $\rho \in (-\infty, +\infty)$. The 3-D Radon transform R of an object $f(\vec{x})$ is defined as plane integrals:

$$R(\hat{\theta}, \rho) = \iiint_{-\infty}^{+\infty} f(\vec{x}) \delta(\vec{x} \cdot \hat{\theta} - \rho) d\vec{x} \tag{6}$$

where the $\delta$ function constrains the 3-D integration in the plane $\zeta(\hat{\theta},\rho)$. The object function $f(\vec{x})$ can be exactly reconstructed by using the inverse 3-D Radon transform:

$$f(\vec{x}) = -\frac{1}{4\pi^2} \int_0^\pi d\varphi \int_0^\pi d\theta \sin\theta \left[ \frac{\partial^2}{\partial \rho^2} R(\hat{\theta}, \rho) \right]\bigg|_{\rho=\vec{x}\cdot\hat{\theta}}, \quad (7)$$

if $R(\hat{\theta},\rho)$ is known for every $(\hat{\theta},\rho)$ on set M:

$$M \triangleq \{(\hat{\theta}, \rho) \mid \theta \in [0, \pi), \varphi \in [0, \pi), \rho \in (-\infty, +\infty)\}.$$

Thus, in cone-beam tomography, the 3-D reconstruction of the object function $f(\vec{x})$ from its cone-beam projection data can be accomplished if the relationship is established between those projections and the object's 3-D Radon transform R.

P. Grangeat, in his work entitled "Mathematical framework of cone-beam 3-D reconstruction via the first derivative of the radon transform," *Mathematical Methods in Tomography*, G. T. Herman, A. K. Lous, F. Natterer, Eds., Lecture Notes in mathematics, Springer Verlag, 1990, developed an exact formula in establishing the relationship between the cone-beam projections $g(\vec{\Phi}, \hat{\beta})$ of the object function $f(\vec{x})$ and the first derivative of its 3-D Radon transform $R(\hat{\theta},\rho)$. That formula is introduced here based on the coordinate systems defined in this specification.

Figure 4:
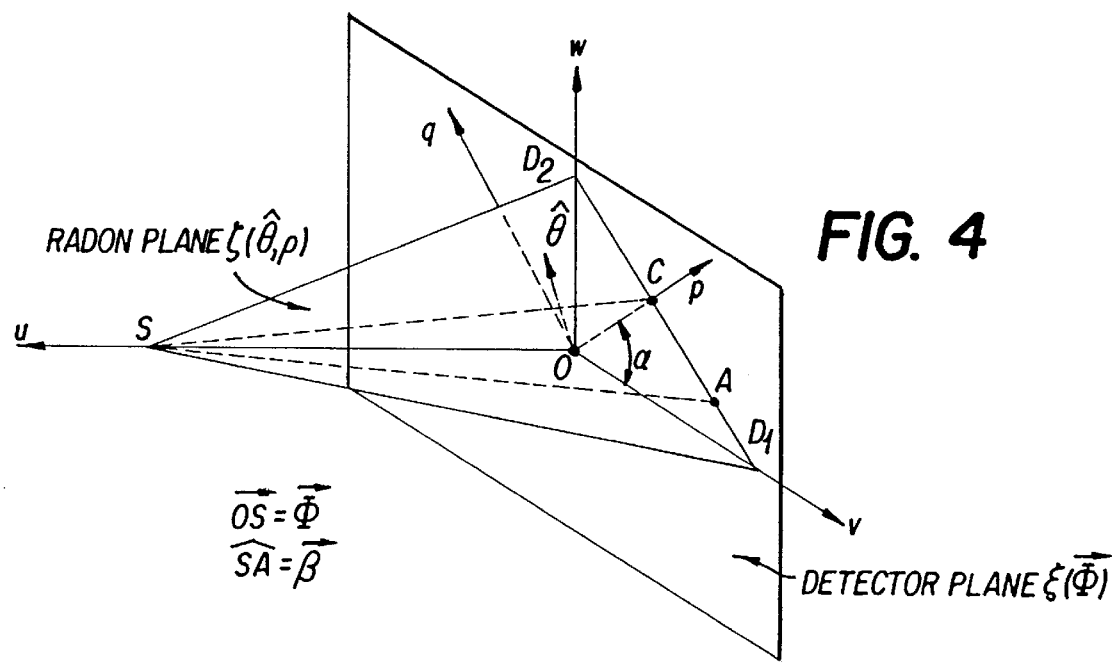
FIG. 4 is a drawing the cone-beam geometry showing the intersection of a Radon plane.

Referring now to FIG. 4, the detector plane $\xi$ is defined in such a way that $\xi$ is perpendicular to the vector $\vec{OS}=(\vec{\Phi})$ and always contains the point O, which is the origin of the coordinate system shown in FIGS. 2 and 4. Therefore, the plane $\xi$ is uniquely defined by the vector $\vec{\Phi}$, i.e., $\xi=\xi(\vec{\Phi})$.

The orientations of the v-axis and the w-axis of the local detector coordinate system uvw-O are arbitrary but normally they take the physical orientations of the detector arrays. The Radon plane $\zeta(\hat{\theta},\rho)$, where the plane integral takes place, goes through the focal point S and intersects the detector plane $\xi(\vec{\Phi})$ at line $D_1D_2$.

As shown in FIG. 4, another local Cartesian coordinate system upq-O is defined with the rotation of the v-axis and the w-axis about the u-axis by an angle $\alpha$, where $\alpha \epsilon$ [$-\pi/2$, $+\pi/2$). The p-axis should be perpendicular to the line $D_1D_2$ and their intersection point is C. Point A can be located anywhere on the line $D_1D_2$ and is assigned the coordinate (0, p, q) in the upq-O coordinate system. Therefore, the projection of the object function $f(\vec{x})$ along the line SA can be expressed in the local upq-O coordinates as:

$$g_{upq-O}(\Phi, p, q) = \int_{-\infty}^{+\infty} f\left(\vec{\Phi} + \frac{\vec{SA}}{|\vec{SA}|} t\right) dt. \quad (8)$$

Having defined the cone-beam geometry and 3-D Radon plane, Grangeat's formula can be expressed as:

$$\frac{\partial}{\partial \rho} R(\hat{\theta}, \rho) = \frac{|\vec{SC}|^2}{|\vec{SO}|^2} \frac{\partial}{\partial p} \int_{-\infty}^{+\infty} \frac{|\vec{SO}|}{|\vec{SA}|} g_{upq-O}(\vec{\Phi}, p, q) dq. \quad (9)$$

Both $\vec{\Phi}$ and p in Equation 9 are functions of $\hat{\theta}$ and $\rho$, and the rebinning process is necessary to transform $\vec{\Phi}$ and p to the 3-D Radon space.

Rebinning to the Radon Domain
(1) Preweighting of the Cone-beam Projections

According to Equation 9, a preweighting of the cone-beam projections should be performed prior to the rebinning process. The direct calculation of the preweighting can be achieved by utilizing the local uvw-O coordinate system, which is detector array oriented.

(2) Integration and Partial Derivative

As shown in Appendix A, the relationship between the first derivative and the preweighted cone-beam projections is given by:

$$\frac{\partial}{\partial \rho} R(\hat{\theta}, \rho) = \frac{|\vec{SC}|^2}{|\vec{SO}|^2} \int_{-\infty}^{+\infty} \left[ \cos\alpha \frac{\partial}{\partial v} G_{uvw-O}(\vec{\Phi}, v, w) + \sin\alpha \frac{\partial}{\partial w} G_{uvw-O}(\vec{\Phi}, v, w) \right] dq. \quad (10)$$

Since the partial derivatives $\partial/\partial v\, G_{uvw-O}(\vec{\Phi},v,w)$ and $\partial/\partial w\, G_{uvw-O}(\vec{\Phi},v,w)$ on the right-hand side of Equation 10 need to be calculated only once, the computational complexity is significantly reduced. In implementing the present invention, these partial derivatives are calculated by convoluting (using FFT) a 1-D ramp filter with $G_{uvw-O}(\vec{\Phi},v,w)$ for a fixed $(\vec{\Phi}, w)$ and a fixed $(\vec{\Phi}, v)$, respectively. To get the best results, the ramp filter is first implemented in the spatial domain to avoid any dc-shift and then multiplied with a Hanmming window in the frequency domain to reduce the reconstruction noise. A line integral algorithm based on a linear interpolation between pixels is applied to Equation 10 for the integration calculations, as shown in the article by Y. Weng, et al. entitled "A Reconstruction Algorithm for Helical Cone-Beam SPECT," *IEEE Transactions in Nuclear Science*, Vol. 40, No. 4, pp. 1092–1101, August 1993.

(3) The Rebinning Process

The rebinning process maps the results on the right-hand side of Equation 10 to the Radon space, i.e., from uvw-O coordinates to $(\vec{\Phi},p)$ coordinates. A unit vector $\hat{\theta}$ can be expressed by two scalar parameters $\theta$ and $\phi$, as in Equation 5; thus the Radon space can be represented by the three scalars $\theta$, $\phi$ and p. In this specification, $\theta$, $\phi$ and p are all linearly quantized into 256 levels in the domain M+e,dus $\Delta$ { $(\hat{\theta}, \rho)|\theta\epsilon[0, \pi), \phi\epsilon[0, \pi), \rho\epsilon(-R, +R)$}. Each point $(\theta, \phi, p)$ in the Radon domain is then mapped back to the projection domain $(\vec{\Phi},v,w)$ and interpolation is accomplished in the projection domain. For that purpose, a new set of rebinning equations have been derived for the circle and arc orbit separately. In the above-cited article, Weng et al. have suggested one method in which the parameters p, $\alpha$ and $\beta$ are discrete and the interpolation is accomplished in the 3-D Radon space. While such a process is appropriate to a helical orbit and can reduce the computational load, it is not suitable to the circle-plus-arc orbit geometry of the present invention because the finite quantization levels of p, $\alpha$ and $\beta$ will introduce large discontinuities in the Radon domain and therefore severe artifacts will be shown in the reconstructed images.

(a) Rebinningfrom the Circular Orbit

Figure 5:
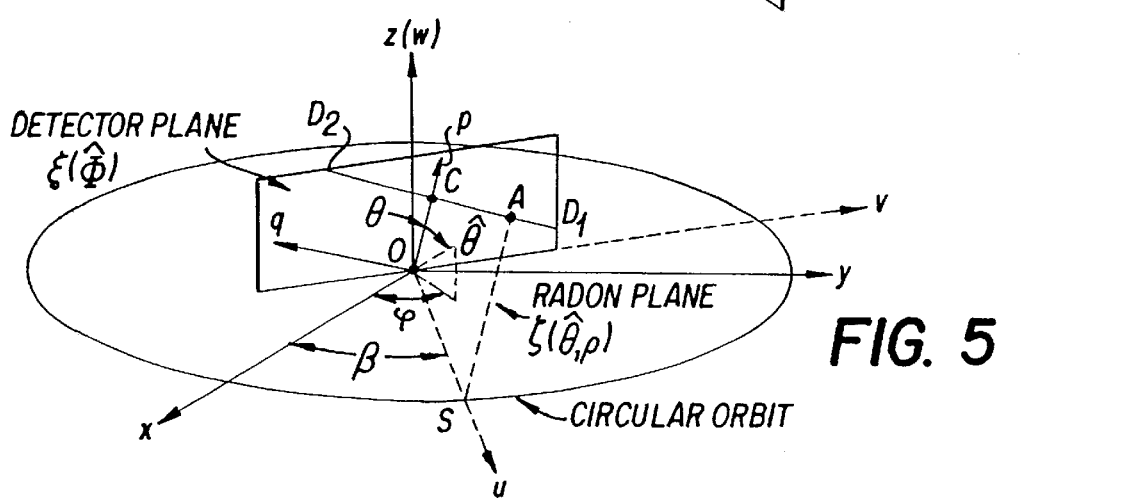
FIG. 5 is a diagram showing projection data taken from the circular orbit.

As shown in FIG. 5, any Radon plane that intersects the circular orbit has two intersection points, except when the Radon plane is tangential to the circular orbit. Either intersection point represents a corresponding focal point position. In order to improve the quality of the reconstructed images, both projections from the two focal points are used. First, the two intersection points are named $B_1$ and $B_2$, respectively, and the position arrangement for $B_1 \rightarrow B_2 \rightarrow O$ is counter-clockwise. Second, the angle between $\overrightarrow{OB}_1$ and the x-axis is $\beta_1$ and that between $\overrightarrow{OB}_2$ and the x-axis is $\beta_2$. Then, for a given point $(\theta, \phi, p)$ in the Radon space, $\beta_1$ and $\beta_2$ can be calculated directly from the coordinates of point $B_1$ and point $B_2$, respectively. As derived in Appendix B, p and $\alpha$ can be solved exactly for a given $\theta$, $\phi$ and p: for $\beta_1$:

$$p = \frac{D|\rho|}{\sqrt{D^2 - \rho^2}}, \tag{11a}$$

$$\alpha = \begin{cases} \sin^{-1}\left(\frac{D\cos\theta}{\sqrt{D^2 - \rho^2}}\right) & \text{for } \rho \geq 0, \\ -\sin^{-1}\left(\frac{D\cos\theta}{\sqrt{D^2 - \rho^2}}\right) & \text{for } \rho < 0, \end{cases} \tag{11b}$$

and for $\beta_2$:

$$p = -\frac{D|\rho|}{\sqrt{D^2 - \rho^2}}, \tag{12a}$$

$$\alpha = \begin{cases} -\sin^{-1}\left(\frac{D\cos\theta}{\sqrt{D^2 - \rho^2}}\right) & \text{for } \rho \geq 0, \\ \sin^{-1}\left(\frac{D\cos\theta}{\sqrt{D^2 - \rho^2}}\right) & \text{for } \rho < 0, \end{cases} \tag{12b}$$

Consequently, if $\theta$, $\phi$, $\rho$ and $\beta$ are discrete parameters, for a given $(\theta, \phi, \rho)$ in the Radon space, only a 1-D interpolation relative to $\beta$ needs to be calculated for the rebinning process, which greatly reduces the interpolation errors. From the above solutions, to find the region where the projection data from the circular orbit can contribute to the Radon space:

$$|\cos\theta| = \tag{13}$$

$$\frac{D\sin\alpha}{\left|\sqrt{D^2 + \rho^2}\right|} \leq \frac{D}{\sqrt{D^2 + \rho^2}} = \frac{\sqrt{D^2 - \rho^2}}{D} \text{ for } \alpha \in \left[-\frac{\pi}{2}, \frac{\pi}{2}\right),$$

i.e., $$\theta_c \leq \theta \leq \pi - \theta_c, \text{ where } \theta_c = \cos^{-1}\left(\frac{\sqrt{D^2 - \rho^2}}{D}\right),$$

which is the mathematical proof why a single circular orbit does not satisfy Tuy's data sufficient condition.

(b) Rebinning from the Arc Orbit

From Equation 13, it can be seen that the region of the Radon space that the projection data can contribute to the arc orbit is:

$$\theta \leq \theta < \theta_c \text{ or } \theta_c < \theta < \pi, \text{ where } \theta_c = \cos^{-1}\left(\frac{\sqrt{D^2 - \rho^2}}{D}\right), \tag{14}$$

Figure 6:
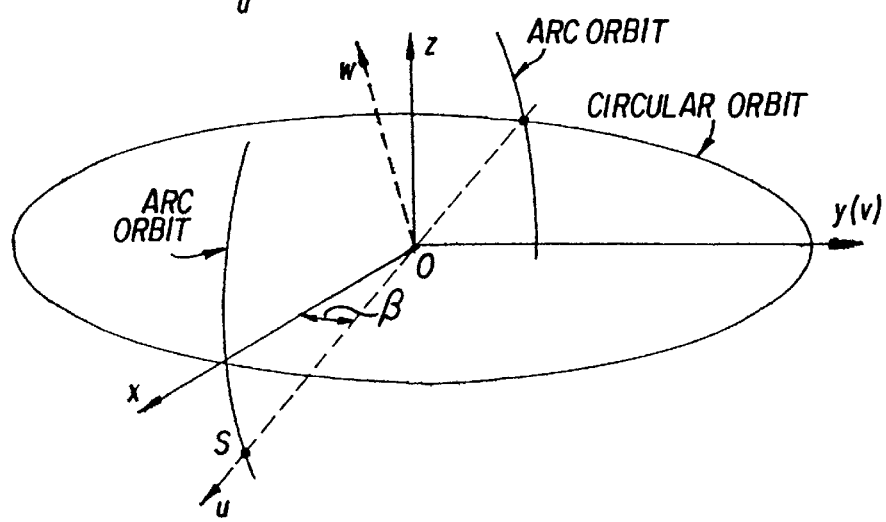
FIG. 6 is a diagram showing projection data taken from the arc orbits.

Referring to FIG. 6, it is seen that the arc orbit comes with the rotation of the focal point S about the y-axis by an angle $\beta$ and $\overrightarrow{OS}$ is defined as the u-axis. As derived in Appendix C, p and $\alpha$ can be solved exactly for a given $(\theta, \phi, \rho)$:

$$p = \frac{D\rho}{\sqrt{D^2 - \rho^2}}, \tag{15a}$$

$$\alpha = \sin^{-1}\left(\frac{\frac{D}{\sqrt{D^2 + \rho^2}}\sin\theta\cos\varphi - \frac{\rho}{\sqrt{D^2 - \rho^2}}\cos\beta}{\sin\beta}\right). \tag{15b}$$

Once again, only the 1-D interpolation with regard to $\beta$ needs to be calculated for the discrete values of the parameters $\theta$, $\phi$, $\rho$ and $\beta$.

(4) Reconstruction of the Object Function

After the first derivative of the Radon transform $\partial/\partial\rho$ $R(\hat{\theta},\rho)$ is obtained from the rebinning process, the calculation of the second derivative can be accomplished by convoluting $\partial/\partial\rho$ $R(\hat{\theta},\rho)$ with a 1-D ramp filter. In order to obtain the best results, the ramp filter is first implemented in the spatial domain to avoid a dc-shift and then multiplied with a Hamming window in the frequency domain in order to reduce the reconstruction noise. The object function can then be reconstructed by using backprojection as indicated in Equation 7.

Figure 8:
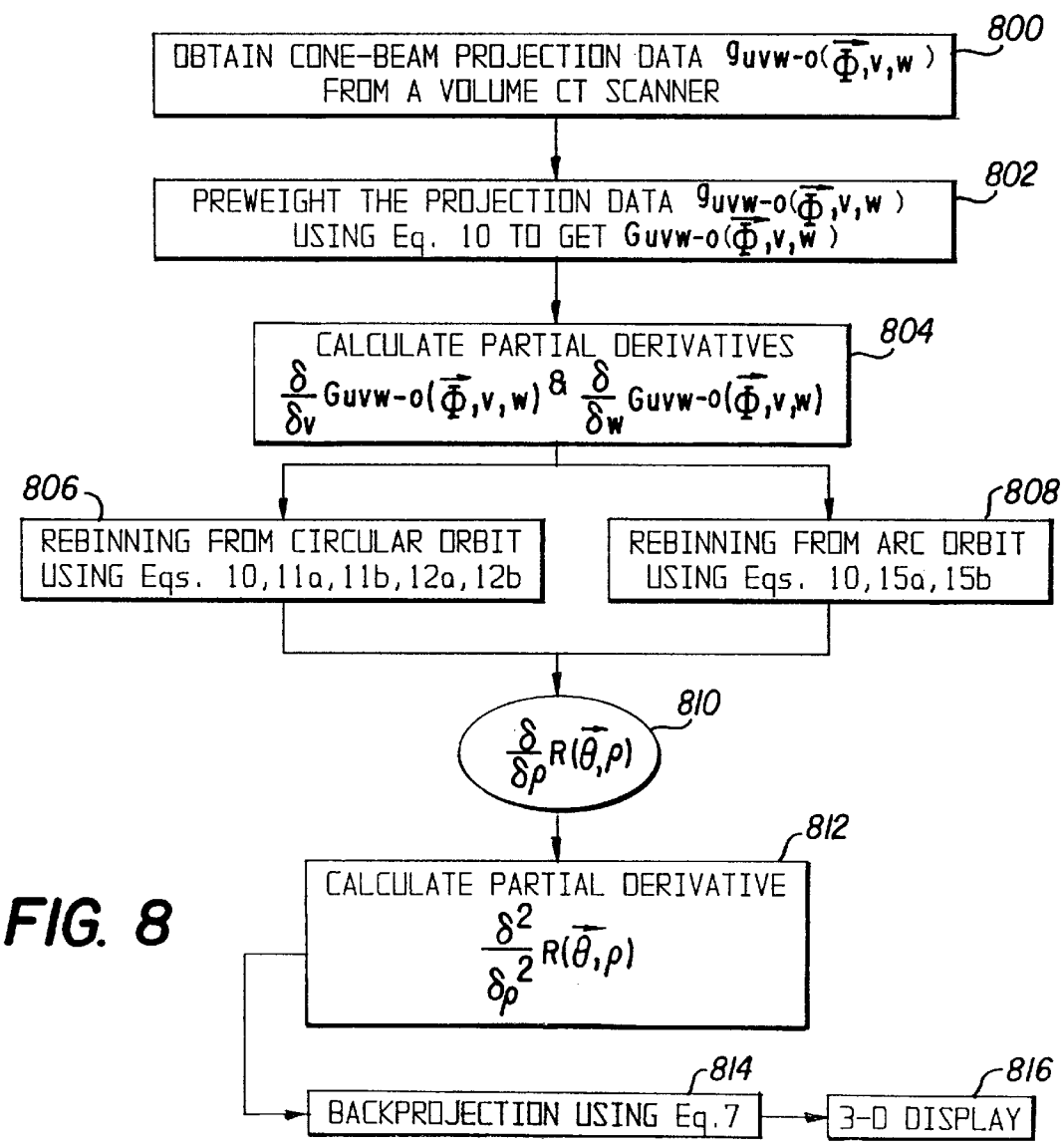
FIG. 8 is a diagram of a flow chart showing the steps performed in converting the projection data from a volume CT scanning apparatus to the cone-beam reconstruction matrix and a desired 3-D tomography display.

Referring now to FIG. 8, which is a diagram of a flow chart showing the steps performed in converting the projection data from a CT scanning apparatus to the desired 3-D display, in the first step 800, the cone-beam projection data is obtained from a volume CT scanner. Then, the projection data $g_{uvw-O}(\overrightarrow{\Phi},v,w)$ is preweighted using Equation 10 in order to obtain the preweighted projection data $G_{uvw-O}(\overrightarrow{\Phi},v,w)$ in Step 802. Then, at Step 804, the partial derivatives $\partial/\partial v$ $G_{uvw-O}(\overrightarrow{\Phi},v,w)$ and $\partial/\partial w$ $G_{uvw-O}(\overrightarrow{\Phi},v,w)$ are calculated. In Step 806, the results from the partial derivatives obtained in Step 804 are used to rebin the data from the circular orbit, using Equations 10, 11a, 11b, 12a and 12b. At Step 808, the partial derivatives calculated in Step 804 are used to rebin data from the arc orbit, using Equations 10, 15a and 15b.

In Step 810, the results from the rebinning from the circular and arc orbits are utilized to obtain the partial derivatives $\partial/\partial p$ $R(\hat{\theta},\rho)$. Next, the partial second derivative $\partial^2/\partial p^2$ $R(\hat{\theta},\rho)$ is calculated at Step 812. Then, at Step 814, the back projection data is calculated, using Equation 7. Finally, at Step 816, the 3-D image is displayed.

Figure 9:
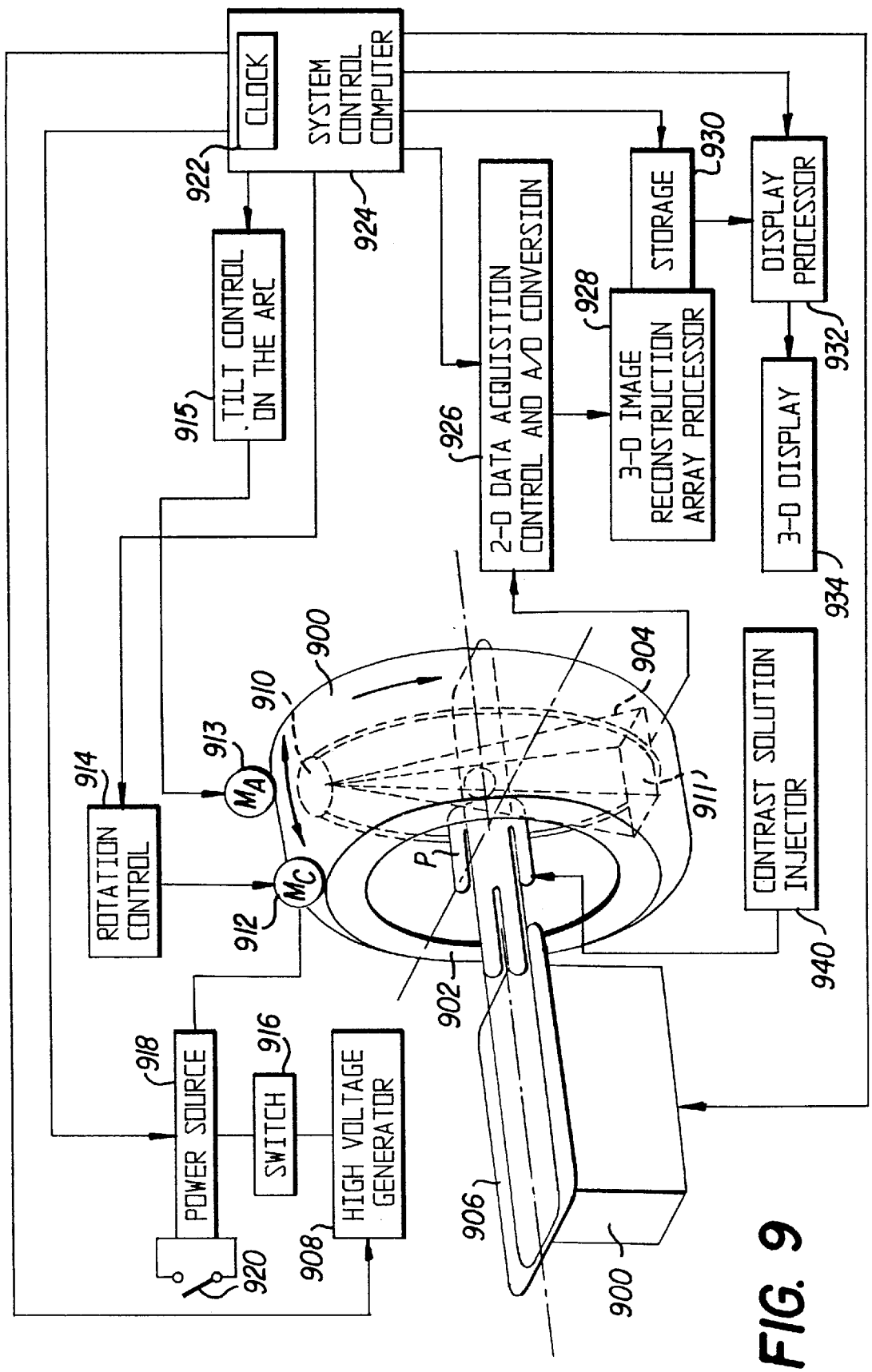
FIG. 9 is a schematic block diagram showing the use of the invented volume CT scanning system.

In a standard CT, a 3-D reconstruction is obtained by stacking a series of slices. In a volume CT, a direct reconstruction of an object can be obtained. Referring now to FIG. 9, it is shown how the cone-beam tomography system 900 of the present invention can be used to obtain a direct 3-D reconstruction of an object. It should be understood that the volume CT scanning apparatus 900 is illustrated in a simplified block diagram form. The invention may preferably be employed in conjunction with such a volume CT scanning apparatus to generate a 3-D reconstruction matrix of the object. Based on the 3-D reconstruction matrix, the desired three dimensional display can be obtained.

A volume CT scanning apparatus examines a body P using a cone shaped radiation beam 904 which traverses a set of paths across the body. As shown in FIG. 9, an x-ray source 910 and a 2-D detector 911 are mounted on a gantry frame 902 that rotates around the body P being examined. The operating voltage for the x-ray source is obtained from a conventional high-voltage generator 908 in such a manner that the x-ray source 910 produces the desired cone-shaped beam of radiation when the high-voltage is applied to it. The high-voltage generator 908 is energized by means of a power source 918, through a switch 916.

A first motor 912 is also powered by the power source 918 such that it drives the gantry frame 902 in its orbit about the body, for example, in a clockwise direction as shown by the arrows adjacent to the frame. The power source 918 is turned on by means of switch 920 or other conventional control devices, in order to initiate a measurement sequence. A speed control circuit 914 is used to control the speed of rotation of the gantry frame 902 and to provide an output control signal which indicates when the speed of the motor 912 is at the desired level for taking measurements. The output from the rotational control 914 may also be utilized to operate the switch 916 such that the high-voltage generator 908 is only turned on when the gantry frame 902 is driven at the desired speed for making measurements.

In order to obtain the arc measurements as previously discussed, a tilt control 915 is utilized to cause the gantry frame 902 to tilt by a relatively small angle of ±15° to ±30°, by means of the gantry frame tilt motor 913. That tilting allows the acquisition of arc projection data on the perpendicular arc. Such geometry results in a complete set of data for an object with a 25–40 cm diameter corresponding to a 37–60 cm field at the detectors 911 with a magnification of 1.5. Although the tilting of the gantry 902 is generally available in a standard CT gantry, to acquire arc projections, the minimal modification of a standard CT gantry has to be made such that the tilting of the gantry, x-ray esure timing and the projection acquisition are synchronized by the system control computer 924 as shown in FIG. 9.

In addition to the method above to acquire circle and arc projections, alternatively, the circle-plus-arc geometry can be implemented in one of the following two ways. In the first and preferred of the three methods, the gantry 902 is tilted to a small angle (±15° to ±30°) and then the x-ray tube 910 and the 2-D detector 911 are rotated while the gantry 902 is tilted. A half set of arc projections will be acquired only when the x-ray tube 910 and the 2-D detector 911 are at the rotation angle of 0°. When the tilted angle becomes zero, the circle projections will be acquired at the preset rotation angle positions. When the circle projection acquisition is completed, the gantry 902 will be tilted toward −15° to −30°. Another half set of arc projections will be acquired only when the x-ray tube 910 and the 2-D detector 911 are at the rotation angle of 0°.

The second alternative method is to mechanically modify a standard CT gantry such that two short arc orbits are added to the gantry, and the x-ray tube 910 and the 2-D detector 911 can be moved on the arc to acquire the arc projections and on the circle to acquire the circle projections. One arc constitutes the orbit of the x-ray tube 910 and the other arc is the orbit of the 2-D detector 911. The two arc orbits are mounted 180° apart from each other, as shown in FIG. 6. The x-ray tube 910 and the 2-D detector 911 are synchronously moved on the arc orbits to acquire arc projections. Then, the x-ray tube 910 and the 2-D detector 911 are rotated on the gantry to acquire circle projections.

Mounted on the gantry frame 902 opposite the x-ray source 910 is a 2-D detector 911 which has a dynamic range equal to or greater than 1000:1 and an image lag of less than 10%, for example a selenium thin film transistor (STFT) array or a silicon STFT array, in order to provide 2-D projections that correspond to an x-ray attenuation signal pattern. The x-ray source 910 and the 2-D detector 911 are mounted on the gantry frame 902 in such a manner that they both move synchronously.

The cone-shaped beam of radiation 904 generated by the x-ray source 910 is projected through the body or object under test. The 2-D detector cone measures the radiation transmitted along the set of beam paths across the cone.

Alternatively, a continuous series of two-dimensional detectors (not shown) can be fixedly mounted proximate to the gantry frame 902 and the x-ray source 910 is mounted to the gantry frame such that, upon rotation of the gantry frame, the cone-shaped radiation beam 904 is projected through the body P under test and sequentially received by each of the series of detectors.

A 2-D projection acquisition control and A/D conversion unit 926, under control of the scanning pulses sequentially obtained from the system control computer 924, which includes the clock 922, receives a sequence of outputs corresponding to different lines of the 2-D detector 911. Each line of the 2-D detector consists of many detection cells (at least >100). The output of each detector cell represents a line integral of attenuation values measurable along one of the respective beam paths. The cone-shaped beam 904 subtends a cone angle sufficient to include the entire region of interest of the body. Thus, a complete scan of the object can be made by merely orbiting the gantry frame 902 supporting the x-ray source 910 and the 2-D detector 911 around the body to acquire the 2-D projection signals at different angular positions.

The analog-to-digital conversion unit 926 serves to digitize the projection signals and to save them in the 3-D image reconstruction array processor 928 and storage device 930. The method employed by the 3-D image reconstruction array processor 928 is the invented algorithm described in this application. The 3-D image reconstruction array processor 928 serves to transform the digitized projection signals into x-ray attenuation data vectors. The x-ray attenuation data matrix corresponds to x-ray attenuation at spaced grid locations within the body trunk being examined. Each data element of the matrix represents an x-ray attenuation value and the location of the element corresponds to a respective 3-D grid location within the body.

In accordance with the principles of the invention discussed previously, a display processor 932 obtains the data stored as 3-D x-ray attenuation signal patterns in the memory storage 930, processes that data as previously described, for example, in connection with FIG. 8, and then the desired 3-D images are displayed on a 3-D display device 934.

The 3-D image reconstruction array processor 932 may, for example, be comprised of an ULTRA SPARC-1 model workstation, available from Sun Microsystems, Inc. of Mountain View, Calif. 94043.

Although only a preferred embodiment is specifically illustrated and described herein, it will be readily appreciated that many modifications and variations of the present invention are possible in light of the above teachings and within the purview of the appended claims without departing from the spirit and intended scope of the invention.

APPENDIX A

With the relationship between the upq-O and the uvw-O coordinate systems (See FIG. 4), $$\begin{pmatrix} u \\ v \\ w \end{pmatrix} = \begin{pmatrix} 1 & 0 & 0 \\ 0 & \cos\alpha & -\sin\alpha \\ 0 & \sin\alpha & \cos\alpha \end{pmatrix} \begin{pmatrix} u \\ p \\ q \end{pmatrix}, \tag{16}$$

and variable substituting, $$\frac{\partial}{\partial p} G_{upq-O}(\vec{\Phi}, p, q) = \frac{\partial v}{\partial p} \frac{\partial}{\partial v} G_{uvw-O}(\vec{\Phi}, v, w) + \quad (17)$$

$$\frac{\partial w}{\partial p} \frac{\partial}{\partial w} G_{uvw-O}(\vec{\Phi}, v, w)$$

$$= \cos\alpha \frac{\partial}{\partial v} G_{uvw-O}(\vec{\Phi}, v, w) +$$

$$\sin\alpha \frac{\partial}{\partial w} G_{uvw-O}(\vec{\Phi}, v, w).$$

As is known in the prior art, great computational efficiency and accuracy can be obtained by swapping the integral with the derivative in Equation 9. With Equation 10 in mind, by putting Equation 17 into Equation 9 and swapping the integral with the derivative, $$\frac{\partial}{\partial \rho} R(\vec{\theta}, \rho) = \frac{|\vec{SC}|^2}{|\vec{SO}|^2} \frac{\partial}{\partial p} \int_{-\infty}^{+\infty} \frac{|\vec{SO}|}{|\vec{SA}|} G_{upq-O}(\vec{\Phi}, p, q) dq \quad (18)$$

$$= \frac{|\vec{SC}|^2}{|\vec{SO}|^2} \frac{\partial}{\partial p} \int_{-\infty}^{+\infty} G_{upq-O}(\vec{\Phi}, p, q) dq$$

$$= \frac{|\vec{SC}|^2}{|\vec{SO}|^2} \int_{-\infty}^{+\infty} \left[\frac{\partial}{\partial p} G_{upq-O}(\vec{\Phi}, p, q)\right] dq$$

$$= \frac{|\vec{SC}|^2}{|\vec{SO}|^2} \int_{-\infty}^{+\infty} \left[\cos\alpha \frac{\partial}{\partial v} G_{uvw-O}(\vec{\Phi}, v, w) + \sin\alpha \frac{\partial}{\partial w} G_{uvw-O}(\vec{\Phi}, v, w)\right] dq.$$

Since the partial derivatives $\partial/\partial v\, G_{uvw-O}(\vec{\Phi},v,w)$ and $\partial/\partial w\, G_{uvw-O}(\vec{\Phi},v,w)$ on the right-hand side of Equation 18 need to be calculated only once, the computational complexity is significantly reduced.

APPENDIX B

To fill the Radon cube $(\theta, \phi, \rho)$ with the projection data from the circular orbit, the transformation function should be found between the local uvw-O coordinates and the absolute xyz-O coordinates (see FIG. 5). The circular orbit lies in the xy plane and the focal point S will be restrained on this orbit. The angle between the x-axis and the vector $\vec{OS}$ is defined as $\beta$ and the angle between the p-axis and the v-axis is $\alpha$. If the point C is represented by $(0, p, 0)$ in the local upq-0 coordinate system, the Radon plane which contains the line $D_1D_2$ and the point S can be described in the uvw-O coordinate system as:

$$up + vD\cos\alpha + wD\sin\alpha - Dp = 0. \quad (19)$$

Referring to FIG. 5, the transformation between the local uvw-O coordinates and absolute xyz-O coordinates can be expressed as:

$$\begin{pmatrix} u \\ v \\ w \end{pmatrix} = \begin{pmatrix} \cos\beta & \sin\beta & 0 \\ -\sin\beta & \cos\beta & 0 \\ 0 & 0 & 1 \end{pmatrix} \begin{pmatrix} x \\ y \\ z \end{pmatrix}. \quad (20)$$

Therefore, the Radon plane represented by Equation 19 can be rewritten in the absolute xyz-O coordinates in terms of the parameters $\alpha$, $\beta$ and p as:

$$x(-D\cos\alpha\sin\beta + p\cos\beta) + y(D\cos\alpha\cos\beta + p\sin\beta) + zD\sin\alpha - Dp = 0. \quad (21)$$

Comparing Equation 21 with the other representation of this Radon plane in terms of $\theta$ and $\rho$:

$$x\sin\theta\cos\phi + y\sin\theta\sin\phi + z\cos\theta - \rho = 0, \quad (22)$$

it can be shown that:

$$\sin\theta\cos\varphi \sim \frac{-D\cos\alpha\sin\beta + p\cos\beta}{\sqrt{D^2 + p^2}}, \quad (23a)$$

$$\sin\theta\sin\varphi \sim \frac{-D\cos\alpha\cos\beta + p\sin\beta}{\sqrt{D^2 + p^2}}, \quad (23b)$$

$$\cos\theta \sim \frac{D\sin\alpha}{\sqrt{D^2 + p^2}}, \quad (23c)$$

$$\rho \sim \frac{Dp}{\sqrt{D^2 + p^2}}. \quad (23d)$$

The symbol "~" is used instead of "=" in Equations 23a–23d because there may be a factor +1 or –1 involved. Any Radon plane (Equation 21) that intersects the circular orbit ($x^2 + y^2 = D^2$) has two intersection points except when the Radon plane is tangential to the circular orbit. Either point represents its corresponding focal point position. In order to improve the quality of the reconstructed images, both projections from the two focal points are used. First, the two intersection points are named $B_1$ and $B_2$ respectively, and the position arrangement for $B_1 \rightarrow B_2 \rightarrow O$ is counter-clockwise. Second, the angle between $\vec{OB_1}$ and the x-axis is $\beta_1$ and that between $\vec{OB_2}$ and the x-axis is $\beta_2$. Then, for a given point $(\theta, \phi, \rho)$ in the Radon space, $\beta_1$ and $\beta_2$ can be calculated directly from the coordinates of point $B_1$ and $B_2$, respectively. The solutions to Equations 23a–23d can also be expressed as: for $\beta_1$:

$$p = \frac{D|\rho|}{\sqrt{D^2 - \rho^2}}, \quad (24a)$$

$$\alpha = \begin{cases} \sin^{-1}\left(\frac{D\cos\theta}{\sqrt{D^2 - \rho^2}}\right) & \text{for } \rho \geq 0, \\ -\sin^{-1}\left(\frac{D\cos\theta}{\sqrt{D^2 - \rho^2}}\right) & \text{for } \rho < 0. \end{cases} \quad (24b)$$

and for $\beta_2$:

$$p = -\frac{D|\rho|}{\sqrt{D^2 - \rho^2}}, \quad (24c)$$

$$\alpha = \begin{cases} -\sin^{-1}\left(\frac{D\cos\theta}{\sqrt{D^2 - \rho^2}}\right) & \text{for } \rho \geq 0, \\ \sin^{-1}\left(\frac{D\cos\theta}{\sqrt{D^2 - \rho^2}}\right) & \text{for } \rho < 0. \end{cases} \quad (24d)$$

Therefore, if $\theta$, $\phi$, $\rho$ and $\beta$ are discrete parameters, for a given $(\theta, \phi, \rho)$ in the Radon space, only a 1-D interpolation relative to β need be calculated, which greatly reduces the interpolation errors.

APPENDIX C

Figure 7:
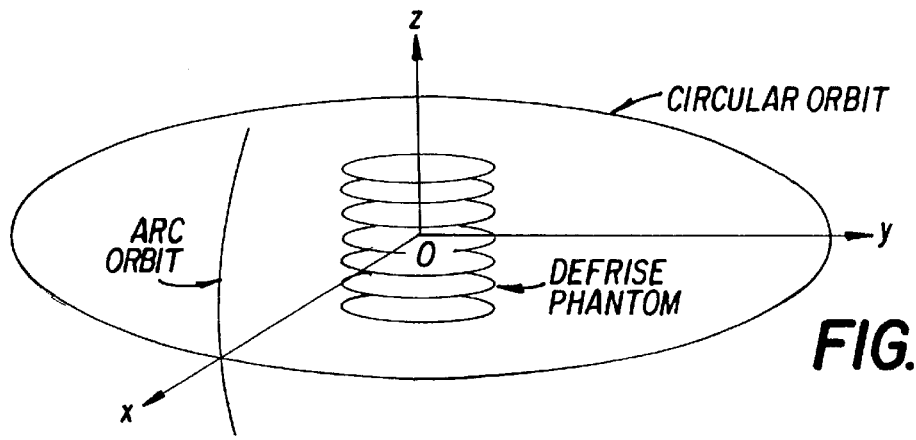
FIG. 7 is a drawing of the geometry of a Defrise Phantom and circle-plus-arc orbit.

Referring to FIG. 7, the arc orbit comes with the rotation of the focal point S about the y-axis by an angle β and $\overrightarrow{OS}$ is defined as the u-axis. The transformation between the local uvw-O coordinate system and the absolute xyz-O coordinate system can be expressed as:

$$\begin{pmatrix} u \\ v \\ w \end{pmatrix} = \begin{pmatrix} \cos\beta & 0 & -\sin\beta \\ 0 & 1 & 0 \\ \sin\beta & 0 & \cos\beta \end{pmatrix} \begin{pmatrix} x \\ y \\ z \end{pmatrix}. \quad (25)$$

Again, the Radon plane represented by Equation 19 can be rewritten in the absolute xyz-O coordinates as:

$$x(D \sin\alpha \sin\beta + p \cos\beta) + yD \cos\alpha + y(D \sin\alpha \cos\beta - p \sin\beta) - Dp = 0. \quad (26)$$

Comparison with Equation 22, which is the representation of the Radon plane in terms of parameters $\hat{\theta}$ and ρ, yields the following results:

$$\sin\theta\cos\varphi = \frac{D\sin\alpha\sin\beta + p\cos\beta}{\sqrt{D^2 + p^2}}, \quad (27a)$$

$$\sin\theta\sin\varphi = \frac{D\cos\alpha}{\sqrt{D^2 + p^2}}, \quad (27b)$$

$$\cos\theta = \frac{D\sin\alpha\cos\beta - p\sin\beta}{\sqrt{D^2 + p^2}}, \quad (27c)$$

$$\rho = \frac{Dp}{\sqrt{D^2 + p^2}}, \quad (27d)$$

Therefore, the solution to the above equations for a given (θ, φ, ρ) are:

$$p = \frac{D\rho}{\sqrt{D^2 - \rho^2}}, \quad (28a)$$

$$\alpha = \sin^{-1}\left(\frac{\frac{D}{\sqrt{D^2 - \rho^2}}\sin\theta\cos\varphi - \frac{\rho}{\sqrt{D^2 - \rho^2}}\cos\beta}{\sin\beta}\right). \quad (28b)$$

Once again, only a 1-d interpolation relative to β needs to be calculated for the discrete values of parameters θ, φ, ρ and β.

We claim:

1. An apparatus for generating a three-dimensional image representative of an interior portion of an object, comprising:

a radiation cone-beam scanner which generates cone-beam projection signals;
 said radiation cone-beam scanner generating cone-beam circular projection signals representative of a circular orbit around said object and cone-beam arc projection signals representative of a plurality of arc orbits about said object;
 means for pre-weighting the cone-beam circular and arc projection signals to produce pre-weighted cone-beam circular and arc projection signals;
 means for calculating the partial derivatives of the pre-weighted cone-beam circular and arc projection signals;
 means for rebinning said pre-weighted cone-beam circular and arc projection signals to produce Radon transform signals;
 means for inverse Radon transforming said Radon transform signals;
 backprojection means for reconstructing the Radon transform signals into a three-dimensional image representation; and an image memory means for storing said three-dimensional image representation.

2. The apparatus of claim 1, wherein said radiation cone-beam scanner is an volume CT scanner.

3. The apparatus of claim 1, wherein said radiation cone-beam scanner is a volume SPECT scanner.

4. The apparatus of claim 1, wherein said radiation is x-rays.

5. The apparatus of claim 1, wherein said plurality of arc orbits are perpendicular to said circular orbit.

6. The apparatus of claim 1, further including a monitor means for displaying said three-dimensional image representation.

7. The apparatus of claim 1, further including means for processing said stored three-dimensional image representation to generate three-dimensional images and display means for displaying said three-dimensional images.

8. The apparatus of claim 1, wherein the means for rebinning comprises means for (i) rebinning said pre-weighted cone-beam circular projection signals to produce a first derivative of said Radon transform signals, (ii) rebinning said pre-weighted cone-beam arc projection signals to produce said first derivative of said Radon transform signals in regions where said cone-beam circular projection signals cannot contribute to said Radon transform and (iii) obtaining a second derivative of said Radon transform signals from said first derivative of said Radon transform signals.

9. The apparatus of claim 1, further including a two-dimensional detector means for acquiring two-dimensional projections from which to directly reconstruct a three-dimensional object.

10. The apparatus of claim 9, wherein:

said two-dimensional detector means defines a detector plane and has a local detector coordinate system with an origin, a Radon plane intersecting the detector plane to define a line of intersection, the origin and the line of intersection being connected by a p axis which is perpendicular to the line of intersection; and
 the means for rebinning comprises means for rebinning said pre-weighted cone-beam circular and arc projection signals according to the following equations, where D is a radius of the circular orbit, (θ, φ, ρ) is a given point in Radon space, p is a perpendicular distance from the origin to the line of intersection measured along the axis, a is an angular orientation of the p axis relative to the local detector coordinate system, β is an angle of rotation of said scanner relative to a plane of said circular orbit, and $\beta_1$ and $\beta_2$ are two points of intersection of the Radon plane with the circular orbit:

(a) for said pre-weighted cone-beam circular projection signals:

(i) for $\beta_1$:

$$p = \frac{D|\rho|}{\sqrt{D^2 - \rho^2}},$$

$$\alpha = \begin{cases} \sin^{-1}\left(\frac{D\cos\theta}{\sqrt{D^2 - \rho^2}}\right) & \text{for } \rho \geq 0, \\ -\sin^{-1}\left(\frac{D\cos\theta}{\sqrt{D^2 - \rho^2}}\right) & \text{for } \rho < 0, \end{cases}$$

(ii) for $\beta_2$:

$$p = -\frac{D|\rho|}{\sqrt{D^2 - \rho^2}},$$

$$\alpha = \begin{cases} -\sin^{-1}\left(\frac{D\cos\theta}{\sqrt{D^2 - \rho^2}}\right) & \text{for } \rho \geq 0, \\ \sin^{-1}\left(\frac{D\cos\theta}{\sqrt{D^2 - \rho^2}}\right) & \text{for } \rho < 0, \end{cases}$$

(b) for said pre-weighted cone-beam arc projection signals:

$$p = \frac{D\rho}{\sqrt{D^2 - \rho^2}},$$

$$\alpha = \sin^{-1}\left(\frac{\frac{D}{\sqrt{D^2 - \rho^2}}\sin\theta\cos\varphi - \frac{\rho}{\sqrt{D^2 - \rho^2}}\cos\beta}{\sin\beta}\right).$$

11. A volume CT scanning apparatus for generating a three-dimensional image representation of an interior portion of an object, comprising:
a movable support on which the object to be scanned is placed;
a gantry frame which rotates around said interior portion of said object to be scanned in a plane perpendicular to said object;
an x-ray source and a two-dimensional detector mounted 180° apart from each other on said gantry frame such that they rotate synchronously with said gantry frame;
a motor for tilting said gantry frame at an angle away from said perpendicular plane;
means for rotating the gantry frame while the gantry frame is continuously tilted,
means for synchronizing the tilting and rotation of the gantry frame such that the tilting of the gantry frame defines a plurality of arc orbits; and
means for acquiring data signals from said two-dimensional detector and generating a three-dimensional image reconstruction matrix from said acquired data.

12. The apparatus of claim 11, wherein said means for generating said three-dimensional image reconstruction matrix from said acquired data comprises means for:
(a) pre-weighting said data signals obtained while said gantry frame is rotating around said interior portion of said object and pre-weighing said data signals obtained while said gantry frame is tilting at said angle away from said perpendicular plane, thereby obtaining pre-weighted data signals;
(b) calculating partial derivatives of said pre-weighted data signals;
(c) re-binning said pre-weighted data signals to produce a first derivative of Radon transform signals;
(d) obtaining a second derivative of said Radon transform signals from said first derivative of said Radon transform signals; and
(e) generating said three-dimensional image representation from said second derivative of said Radon transform signals.

13. The apparatus of claim 12, wherein said means for generating a three-dimensional image reconstruction transforms projection signals into an x-ray attenuation data matrix.

14. The apparatus of claim 13, wherein each data element in said x-ray attenuation data matrix corresponds to an x-ray attenuation value at a known location within said interior portion of said object.

15. The apparatus of claim 9, further including a display processor connected to said means for generating a desired three-dimensional image display from the three-dimensional image reconstruction matrix.

16. The apparatus of claim 11, wherein said means for acquiring comprises means for:
(a) pre-weighting said data signals obtained while said gantry frame is rotating around said interior portion of said object and pre-weighing said data signals obtained while said gantry frame is tilting at said angle away from said perpendicular plane;
(b) calculating partial derivatives of said pre-weighted data signals;
(c) re-binning said pre-weighted data signals to produce a first derivative of Radon transform signals;
(d) obtaining a second derivative of said Radon transform signals from said first derivative of said Radon transform signals; and
(e) generating said three-dimensional image representation from said second derivative of said Radon transform signals.

17. A method for generating a three-dimensional image representation of an interior portion of an object, comprising the steps of:
scanning said portion of said object using an x-ray source and a two-dimensional detector;
generating a three-dimensional reconstruction matrix of said portion of said object using data signals generated by said two-dimensional detector; and
generating said three-dimensional image using said three-dimensional reconstruction matrix;
wherein said step of scanning generates cone beam circular projection signal representations of a circular orbit around said interior portion of said object and cone-beam arc projection signals representative of a plurality of arc orbits about said interior portion of said object.

18. The method of claim 17, wherein said x-ray source generates a cone-shaped beam of radiation which projects through said interior portion of said object.

19. The method of claim 17, wherein said scanning step is accomplished using a volume CT scanning apparatus having a gantry frame which rotates around said interior portion of said object in a plane perpendicular thereto and in which said gantry frame is further capable of being tilted at an angle away from said perpendicular plane.

20. The method of claim 19, wherein said gantry frame is continuously tilted through a range of angles both positive and negative from said perpendicular plane.

21. The method of claim 20, wherein said range of angles is approximately 15 to approximately 30 degrees.

22. A method for generating a three-dimensional image representation of an interior portion of an object, comprising the steps of:

scanning said portion of said object using an x-ray source and a two-dimensional detector;

generating a three-dimensional reconstruction matrix of said portion of said object using data signals generated by said two-dimensional detector; and generating said three-dimensional image using said three-dimensional reconstruction matrix;

wherein said scanning step is accomplished using a volume CT scanning apparatus having a gantry frame which rotates around said interior portion of said object in a plane perpendicular thereto and in which said gantry frame is further capable of being tilted at an angle away from said perpendicular plane; and wherein said scanning step further includes rotating said gantry frame around said interior portion of said object and tilting said gantry frame while said gantry frame is rotating.

23. A method for generating a three-dimensional image representation of an interior portion of an object, comprising the steps of:

scanning said portion of said object using an x-ray source and a two-dimensional detector, wherein said scanning step utilizes a minimum arc spanning angle and a minimum cone-angle and wherein said minimum arc spanning angle is not less than twice said minimum cone-angle;

generating a three-dimensional reconstruction matrix of said portion of said object using data signals generated by said two-dimensional detector; and generating said three-dimensional image using said three-dimensional reconstruction matrix.

24. A method for generating a three-dimensional image representation of an interior portion of an object, comprising the steps of:

scanning said portion of said object using an x-ray source and a two-dimensional detector;

generating a three-dimensional reconstruction matrix of said portion of said object using data signals generated by said two-dimensional detector; and generating said three-dimensional image using said three-dimensional reconstruction matrix;

wherein said scanning step is accomplished using a volume CT scanning apparatus having a gantry frame which rotates around said interior portion of said object in a plane perpendicular thereto and in which said gantry frame is further capable of being tilted at an angle away from said perpendicular plane, and wherein said scanning step comprises the steps of:

tilting said gantry frame to a predetermined angle away from said plane perpendicular to said interior portion of said object;

rotating said gantry frame and acquiring one-half of the desired arc projection data when said x-ray source and two-dimensional detector are at a plurality of desired rotation angles;

tilting said gantry frame back to said plane perpendicular to said interior portion of said object;

rotating said gantry frame and acquiring the desired circle projection data;

tilting said gantry frame in the same direction it moved in said first tilting step away from said plane perpendicular to said interior portion of said object; and rotating said gantry frame and acquiring the remaining one-half of the desired arc projection data when said x-ray source and two-dimensional detector are at the plurality of desired rotation angles.

25. A volume CT scanning apparatus for generating a three-dimensional image representation of an interior portion of an object, comprising:

a movable support on which the object to be scanned is placed;

a gantry frame which rotates around said interior portion of said object to be scanned in a plane perpendicular to said object;

a series of two-dimensional detectors fixedly mounted proximate to said rotating gantry frame;

an x-ray source mounted on said gantry frame such that it rotates with respect to said series of two-dimensional detectors;

a motor for tilting said gantry frame at an angle away from said perpendicular plane;

means for rotating the gantry frame while the gantry frame is continuously tilted;

means for synchronizing the tilting and rotation of the gantry frame such that the tilting of the gantry frame defines a plurality of arc orbits; and means for acquiring data signals from each said two-dimensional detectors and generating a three-dimensional image reconstruction matrix from said acquired data.

26. A volume CT scanning apparatus for generating a three-dimensional image representation of an interior portion of an object, comprising:

a movable support on which the object to be scanned is placed;

a gantry frame which rotates around said interior portion of said object to be scanned in a plane perpendicular to said object;

an x-ray source and a two-dimensional detector mounted 180° apart from each other on said gantry frame such that they rotate synchronously with said gantry frame, wherein said two-dimensional detector comprises a 2-D detector array having a dynamic range of equal to or greater than 1000:1;

a motor for tilting said gantry frame at an angle away from said perpendicular plane; and means for acquiring data signals from said two-dimensional detector and generating a three-dimensional image reconstruction matrix from said acquired data.

27. A volume CT scanning apparatus for generating a three-dimensional image representation of an interior portion of an object, comprising:

a movable support on which the object to be scanned is placed;

a gantry frame which rotates around said interior portion of said object to be scanned in a plane perpendicular to said object;

an x-ray source and a two-dimensional detector mounted 180° apart from each other on said gantry frame such that they rotate synchronously with said gantry frame, wherein said two-dimensional detector comprises one of a selenium thin film, a silicon thin film transistor array and another two-dimensional digital detector;

a motor for tilting said gantry frame at an angle away from said perpendicular plane; and means for acquiring data signals from said two-dimensional detector and generating a three-dimensional image reconstruction matrix from said acquired data.

* * * * *